(12) United States Patent
Kuwagaki et al.

(10) Patent No.: US 11,548,995 B2
(45) Date of Patent: Jan. 10, 2023

(54) POROUS RESIN MICROPARTICLES AND MANUFACTURING METHOD FOR SAME

(71) Applicant: SEKISUI PLASTICS CO., LTD., Osaka (JP)

(72) Inventors: Kaori Kuwagaki, Nara (JP); Akiyoshi Kusaka, Nara (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 72 days.

(21) Appl. No.: 17/106,518

(22) Filed: Nov. 30, 2020

(65) Prior Publication Data

US 2021/0079190 A1 Mar. 18, 2021

Related U.S. Application Data

(62) Division of application No. 15/762,650, filed as application No. PCT/JP2016/076484 on Sep. 8, 2016, now abandoned.

(30) Foreign Application Priority Data

| Sep. 30, 2015 | (JP) | 2015-193636 |
| Sep. 30, 2015 | (JP) | 2015-193640 |
| Apr. 11, 2016 | (JP) | 2016-078820 |

(51) Int. Cl.
*C08J 9/28* (2006.01)
*C08J 3/14* (2006.01)

(52) U.S. Cl.
CPC . *C08J 9/28* (2013.01); *C08J 3/14* (2013.01); C08J 2329/00 (2013.01)

(58) Field of Classification Search
CPC ....... A61K 8/0283; A61K 9/0002; C08J 3/14; C08J 9/28; C08J 2329/00; C08J 2367/02; C08J 2367/04; C09D 7/65; C09D 7/70
See application file for complete search history.

(56) References Cited

U.S. PATENT DOCUMENTS

| 2002/0156150 A1* | 10/2002 | Williams | C12P 7/625 523/113 |
| 2004/0146540 A1 | 7/2004 | Ueda et al. | |
| 2005/0065318 A1 | 3/2005 | Jernigan et al. | |
| 2012/0321681 A1 | 12/2012 | Gonzales et al. | |
| 2013/0309497 A1 | 11/2013 | Takezaki et al. | |
| 2014/0147726 A1 | 5/2014 | Toyoda | |
| 2014/0308481 A1* | 10/2014 | Mitsui | B01J 6/005 521/182 |
| 2015/0183928 A1 | 7/2015 | Takezaki et al. | |
| 2015/0353707 A1 | 12/2015 | Suzuki et al. | |
| 2016/0130487 A1 | 5/2016 | Iwamoto et al. | |
| 2016/0230039 A1* | 8/2016 | Elias | C08J 5/18 |
| 2016/0257098 A1* | 9/2016 | Nissenbaum | B29C 48/92 |

FOREIGN PATENT DOCUMENTS

| CN | 104324006 | 2/2015 |
| EP | 1 964 879 | 9/2008 |
| EP | 2 537 917 | 12/2012 |
| GB | 2226318 | 6/1990 |
| GB | 2226319 | 6/1990 |
| JP | 2-215838 | 8/1990 |
| JP | 2002-302567 | 10/2002 |
| JP | 2002-363291 | 12/2002 |
| JP | 2004-269865 | 9/2004 |
| JP | 2004-277680 | 10/2004 |
| JP | 2004-277681 | 10/2004 |
| JP | 2005-2302 | 1/2005 |
| JP | 2005-200663 | 7/2005 |
| JP | 2007-246718 | 9/2007 |
| JP | 2009-144012 | 7/2009 |
| JP | 5110225 | 12/2012 |
| JP | 2015-67616 | 4/2015 |
| WO | 2012/105140 | 8/2012 |

OTHER PUBLICATIONS

International Search Report dated Dec. 13, 2016 in International Application No. PCT/JP2016/076484.
Extended European Search Report dated May 29, 2019 in European Patent Application No. 16851082.4.

* cited by examiner

*Primary Examiner* — John M Cooney
(74) *Attorney, Agent, or Firm* — Wenderoth, Lind & Ponack, L.L.P.

(57) ABSTRACT

A manufacturing method for porous resin microparticles comprising steps of: heating a polyester thermoplastic resin having biodegradability to a temperature of 80° C. or higher and 200° C. or lower in a glycol ether solvent to obtain a solution, and cooling the solution to precipitate the polyester thermoplastic resin as porous resin microparticles.

12 Claims, 3 Drawing Sheets

(a)          (b)

(a)  (b)

POROUS RESIN MICROPARTICLES AND MANUFACTURING METHOD FOR SAME

TECHNICAL FIELD

The present invention relates to porous resin microparticles and a manufacturing method for the same.

BACKGROUND ART

To modify and improve quality of various materials, thermoplastic resin particles are used that have a large specific surface and a structure of their own. The materials are mainly used for, for example, compounding agents for cosmetics such as foundation, antiperspirants, and skin scrubs; various agents such as matte coating agents to be used in paints, rheological modifying agents, antiblocking agents, lubricating additives, light diffusing agents, and medical diagnostic testing agents; and additives used for molded articles such as automobile materials and construction materials.

While environmental concerns have been mounting in recent years, materials derived from non-petroleum resources are desired in various fields where use resins so as to reduce burdens on the environment. Of the fields, a field where uses resin particles to be contained in cosmetics, paints and the like also desires such materials.

To manufacture traditional thermoplastic resin particles, various methods have been known. For example, Patent Literature 1 (Japanese Patent Number 5110225) suggests a process of producing small-particle-diameter, highly oil-absorbing, porous, polylactic acid-based resin microparticles by dissolving a polylactic acid and several kinds of resins in an ether-based solvent and then subjecting a mixture to a shearing force to obtain an emulsion, and afterwards making the emulsion contact with a poor solvent. Patent Literature 2 (Japanese Unexamined Patent Publication Number 2007-246718) suggests a method for manufacturing resin powder by dispersing amorphous thermoplastic resin powder in a mixture of a polyalcohol and hydrophobic silica microparticles and then heating and stirring the resultant mixture, and afterwards cooling the mixture. Patent Literature (Japanese Unexamined Patent Publication Number 2015-67616) suggests a method for precipitating polylactic acid microparticles by dissolving a polylactic acid in a first solvent to obtain a solution and then adding a second solvent, which is lower solubility of the polylactic acid than the first solvent, to the solution. Patent Literature 4 (Japanese Unexamined Patent Publication Number Hei 2(1990)-215838) suggests a method for making particles by heating a mixture of a partially-crystallized polyester and an intermediate solvent and then cooling the mixture under conditions allowing a solid phase/liquid phase separation.

As the materials derived from the non-petroleum resources, polylactic acids, which are biodegradable resins, are widely known. A variety of documents describe polylactic acid-containing particles.

Known biodegradable resins other than the polylactic acids are polybutylene succinates, polyhydroxyalkanoates, and the like. Not so many documents describe particles containing any of these resins. One document describing such particles is Japanese Unexamined Patent Publication Number 2002-302567 (Patent Literature 5).

Patent Literature 5 describes pre-expanded particles obtained by cutting a strand of a polybutylene succinate extruded from an extruder.

CITATION LIST

Patent Literatures

[PTL 1] Japanese Patent Number 5110225
[PTL 2] Japanese Unexamined Patent Publication Number 2007-246718
[PTL 3] Japanese Unexamined Patent Publication Number 2015-67616
[PTL 4] Japanese Unexamined Patent Publication Number Hei 2(1990)-215838
[PTL 5] Japanese Unexamined Patent Publication Number 2002-302567

SUMMARY OF INVENTION

Technical Problems

The methods described in Patent Literatures 1 to 4 have not only a problem with productivity due to the necessity of many stages during procedures, such as a dissolution stage, a precipitation stage, and a drying stage, but also a problem with mass generation of impurity-containing solvent waste. This solvent waste is most likely to harm the environment if the waste is discharged into the environment, and a large amount of labor is required if the waste is subjected to a treatment for removing the impurities so as to make the waste reusable. Additionally, it is highly possible that this treatment produces some materials that are likely to harm the environment. Furthermore, the obtained powder is most likely to contain an extremely small amount of the solvent, and this remaining solvent may possibly cause harmful effects on quality of final products. For example, there is some concern over the final products in the field of the cosmetics or the paints that their optical characteristics in particular may not be sufficiently exerted.

In addition, in Patent literature 5, the particles were neither minute nor uniform in particle diameter, since they were obtained by cutting the strand. Also, because of their cylindrical shape, the particles were difficult to meet physical properties (for example, porosity) required by various additives. Therefore, it had been desired that porous microparticles containing the biodegradable resin such as the generally known polylactic acid, and further the polybutylene succinate, or the polyhydroxyalkanoate can be provided in a simple way.

Solution to Problems

The inventors of the present invention had found that porous resin microparticles can be manufactured by using an alcohol solvent as a solvent for dissolving and precipitating a thermoplastic resin, and had achieved the present invention, the alcohol solvent having the following features: low degree of solubility of the resin at normal temperature, high degree of solubility of the resin at high temperatures, having a specific structure, and high in stability.

The present invention can provide a manufacturing method for porous resin microparticles comprising a step of heating a polyester thermoplastic resin having biodegradability to a temperature of 80° C. or higher and 200° C. or lower in a glycol ether solvent to obtain a solution, and cooling the solution to precipitate the polyester thermoplastic resin as porous resin microparticles.

The present invention can also provide porous resin microparticles containing a polybutylene succinate or polyhydroxyalkanoate as a main component.

The present invention can also provide a cosmetic material comprising the porous resin microparticles.

The present invention can also provide a coating material comprising the porous resin microparticles.

The present invention can also provide an absorptive and slow-release formulation comprising the porous resin microparticles.

Advantageous Effects of Invention

The present invention can provide a manufacturing method capable of easily manufacturing porous resin microparticles. By the manufacturing method of the present invention, the porous resin microparticles that are spherical in shape, small-particle-diameter, narrowly-distributed, and excellent in optical characteristics can be manufactured with use of a highly stable alcohol solvent but without using a skin-irritant organic solvent (such as xylene, toluene, n-methylpyrrolidone, chloroform, methylene chloride, dioxolan, or THF) which is normally used to finely grain a thermoplastic resin.

The present invention can also provide porous resin microparticles containing a polybutylene succinate or a polyhydroxyalkanoate as a main component.

The manufacturing method capable of more easily manufacturing the porous resin microparticles can be provided by any of the following approaches:
(1) The polyester thermoplastic resin is at least one kind selected from the group consisting of polylactic acids, polybutylene succinates, polyhydroxyalkanoates, and polycaprolactams.
(2) The glycol ether solvent is 3-alkoxy-3-methyl-1-butanol.
(3) Provided that a melting point of the polyester thermoplastic resin is indicated by T° C., the resin is heated in a range from T−40 to T+40° C.

Moreover, the microscopic, uniformly-sized porous resin microparticles can be provided by any of the following approaches:
(1) The porous resin microparticles contain the polybutylene succinate or the polyhydroxyalkanoate as the main component, and have 1 to 200 µm of a volume average particle diameter (A) determined by a Coulter counter method and 1 to 6 of a particle size distribution index (volume average particle diameter (A)/number average particle diameter (B)).
(2) The porous resin microparticles have 1.1 to 2.0 of a particle form index (circle equivalent diameter (C)/number average particle diameter (B)) that is a ratio between an circle equivalent diameter (C) determined by an image analytical method and a number average particle diameter (B) determined by the Coulter counter method.
(3) The porous resin microparticles have 150 to 350 mL/100 g of a linseed oil absorption amount thereby.

BRIEF DESCRIPTION OF DRAWINGS

FIG. 3 shows photographs of porous resin microparticles in accordance with Example 2a.

FIG. 6 shows a photograph of porous resin microparticles in accordance with Example 10a.

DESCRIPTION OF EMBODIMENTS

Figure 1:
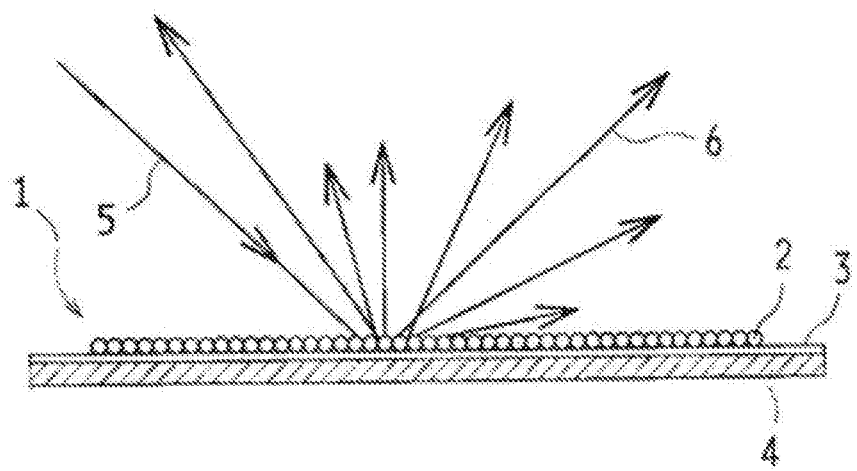
FIG. 1 is a schematic view illustrating how a light scattering index is measured.

The porous resin microparticles of the present invention (hereinafter referred to also as the "porous particles") can be manufactured by way of a step (dissolving step) of heating a polyester thermoplastic resin having biodegradability to a temperature of 80° C. or higher to 200° C. or lower in a glycol ether solvent to obtain a solution, and a step (precipitating step) of cooling the solution to precipitate the polyester thermoplastic resin as porous particles. The heating temperature may be 80° C., 100° C., 120° C., 150° C., 170° C. or 200° C. To manufacture the porous particles containing the polyester thermoplastic resin, such as the polybutylene succinate (PBS) or the polyhydroxyalkanoate (PHA), as the main component, it is desirable to obtain the solution by dissolving a base material resin containing the PBS or the PHA as the main component in the glycol ether solvent during the dissolving step at a temperature of 100° C. or higher to 200° C. or lower. The method of the present invention has an advantage in enabling the biodegradable polyester thermoplastic resin, which is normally difficult to finely grain, to grain easily by wet process.

To be considered the main component, a content may need to be at least 50 wt % or more, preferably 80 wt % or more, and may be 100 wt %.

(1) Polyester Thermoplastic Resin Having Biodegradability

As examples of the polyester thermoplastic resin having the biodegradability (hereinafter referred to also as the "biodegradable resin"), there may be mentioned resins having biodegradability that are usually difficult to grain. It is desirable that the biodegradable resin dissolves in the solvent at high temperatures but does not dissolve at normal temperature. Examples of the resin include a polylactic acid, a polybutylene succinate (PBS), a polyhydroxyalkanoate, and a polycaprolactam. Of the polyhydroxyalkanoates, poly (3-hydroxyalkanoate) polymers or copolymers are preferred that have a repeating unit represented by the general formula (1): —CH(R)—CH$_2$CO—O— wherein R is an alkyl group represented by —C$_n$H$_{2n+1}$ in which n is an integer of 1 to 15. More specifically, the copolymer of 3-hydroxybutylate and at least one kind of a monomer may be used, the monomer being selected from the group consisting of 3-hydroxypropionate, 3-hydroxyvalerate, 3-hydroxyhexanoate, 3-hydroxyheptanoate, 3-hydroxyoctanoate, 3-hydroxynonate, 3-hydroxydecanoate, 3-hydroxytetradecanoate, 3-hydroxyhexadecanoate, 3-hydroxyoctadecanoate, 4-hydroxybutylate, 4-hydroxyvalerate, 5-hydroxyvalerate, and 6-hydroxyhexanoate. Examples of the poly (3-hydroxyalkanoate) polymer or copolymer include a homopolymer of the above-described 3-hydroxyalkanoate, copolymers of two or more kinds of the 3-hydroxyalkanoates in which n is different or composites having two or more kinds selected from the group consisting of the above-described homopolymer, and the above-described copolymer. Of these examples, the homopolymer, the copolymer, and the mixture are preferred that comprise the group consisting of a 3-hydroxybutylate repeating unit in which n=1, a 3-hydroxyvalerate repeating unit in which n=2, a 3-hydroxyhexanoate repeating unit in which n=3, a 3-hydroxyoctanoate repeating unit in which n=5, and a 3-hydroxyoctadecanoate repeating unit in which n=15; and more preferably the copolymer comprising the 3-hydroxybutylate repeating unit and the at least one repeating unit selected from the group consisting of the 3-hydroxyvalerate, the 3-hydroxyhexanoate, and the 3-hydroxyoctanoate. The most preferred copolymer is poly(3-hydroxybutylate-co-3-hydroxyhexanoate) having the 3-hydroxybutylate repeating unit and the 3-hydroxyhexanoate unit. As specific examples of the most preferred copolymer there may be mentioned AONILEX series (product name) manufactured by Kaneka Corporation.

These exemplified resins may be used independently, or two or more kinds may be mixed and used. A molecular weight of the polyester thermoplastic resin having the biodegradability is not particularly limited, and may be properly selected in view of end use or final purposes.

The biodegradable resin may contain any of the following well-known components as needed: a flowability regulator, an ultraviolet absorber, a photostabilizer, a pigment (such as an extender pigment, a color pigment, a metallic pigment, or a mica powder pigment), a dye, etc.

(2) Heating Step

Used as the glycol ether solvent during the heating step is not m particularly limited as long as the biodegradable resin may be heated to a temperature of 80° C. or higher to 200° C. or lower. It is desirable to use the glycol ether solvent that allows the base material resin, which contains the PBS as the main component, to be heated to a temperature of 100° C. or higher to 200° C. or lower.

Examples of the glycol ether solvent include 3-alkoxy-3-methyl-1-butanol and/or 3-alkoxy-3-methyl-1-butyl acetate (the carbon number of the alkoxy group is 1 to 5) (both of which are hereinafter referred to also as the "specific solvents") and propylene glycol monopropyl ether and propylene glycol monomethyl ether (glycol derivatives).

The specific solvents among the glycol ether solvents are suitable for use in cosmetics since the specific solvents are biodegradable and less in skin irritancy, and may not cause any harm by their residues. Additionally, the specific solvents allow the biodegradable resin to dissolve at high temperatures, but do not allow the biodegradable resin to dissolve at normal temperature, with the result that the specific solvents are readily reusable and industrially advantageous. Examples of the alkoxy group include methoxy, ethoxy, propoxy, butoxy, and pentyloxy. The propoxy, the butoxy, and the pentyloxy may be linear but may also be in the form of any structural isomers. The preferred alkoxy group is the methoxy, the ethoxy, or the propoxy. In view of their solubility, 3-alkoxy-3-methyl-1-butanol is preferable, and 3-methoxy-3-methyl-1-butanol is more preferable, among the above-described solvents. Also, used as the specific solvent is Solfit (trade name) that is commercially available from Kuraray Co., Ltd. The specific solvent, 3-alkoxy-3-methyl-1-butanol, may be manufactured by a method described in, for example, WO 2013/146370.

The specific solvent preferably accounts for 50 wt % or more with respect to the glycol ether solvent, more preferably 70 wt % or more, and further preferably 100 wt %. Examples of a usable solvent other than the specific solvents and the glycol derivatives include lower alcohols, such as methanol and ethanol, and acetate ester solvents, such as ethyl acetate and butyl acetate.

An amount of the solvent used is desirably 200 to 20,000 parts by weight with respect to 100 parts by weight of the biodegradable resin. In a case of the solvent less than 200 parts by weight, a concentration of the biodegradable resin becomes too high, possibly leading to a difficulty in stirring and mixing the mixture thoroughly. In a case of the solvent more than 20,000 parts by weight, a yield may be too low compared with a size of equipment. The amount of the solvent is preferably 300 to 10,000 parts by weight, and more preferably 400 to 3,500 parts by weight.

The heating and stirring is carried out at a heating temperature of 80° C. or higher to 200° C. or lower. The base material resin containing the PBS or the PHA as the main component is heated preferably at a heating in temperature of 100° C. or higher to 200° C. or lower. In a case of a heating temperature below 80° C., the biodegradable resin may not possibly soften and may not possibly be finely grained. The heating and stirring may be carried out at a temperature of 200° C. or lower. Provided that a melting point of the biodegradable resin is indicated by T° C., the heating temperature is preferably in a range from T−40 to T+40° C. The heating temperature may be T−40° C., T−20° C., T° C., T+20° C., or T+40° C. In the case where the base material resin contains the PBS or the PHA as the main component, and the melting point of the base material resin is indicated by T° C., the heating temperature is preferably in a range from T−20 to T+40° C.

The porous particles obtained by the manufacturing method of the present invention have a narrow particle size distribution, and the particles may be adequately manufactured as long as the stirring is carried out by a publicly known method. The publicly known method may be a liquid-phase stirring method using stirring blades, a mixing method using a homogenizer, ultrasonic irradiation, or the like.

A stirring speed and a stirring time are not particularly limited as long as the biodegradable resin can be dissolved in the solvent, and it is desirable that the stirring speed and the stirring time may be properly selected.

The heating and stirring is usually carried out under atmospheric pressure, but may be carried out under reduced pressure or under increased pressure as needed.

(3) Cooling Step

To precipitate the biodegradable resin as the particles, the biodegradable resin-containing solvent is cooled after being heated and stirred. A cooling temperature is usually normal temperature (about 25° C.). Faster is better to reach the cooling temperature from the heating and stirring temperature. The cooling is carried out desirably at a speed of −1 to −5° C./min until reaching 25° C.

It is also desirable that the cooling is carried out during the stirring. The stirring speed may be set in the same range as the stirring speed during the heating and stirring.

The porous particles in the cooled solvent may be filtered, dehydrated, and dried as needed before being taken out of the solvent. The filtration, the dehydration, and the drying are not particularly limited, and may be carried out by commonly known methods.

(4) Porous Resin Microparticles

The manufacturing method of the present invention can provide the porous particles having 1 to 200 μm of the volume average particle diameter determined by the Coulter counter method. The manufacturing method of the present invention can also provide the porous particles having 150 to 350 mL/100 g of a linseed oil adsorption amount. At a time of manufacturing products containing the porous particles, the porous particles having the above-described range of the particle diameter and of the linseed oil adsorption amount can improve handleability during blending the porous particles. The above-described range of the linseed oil adsorption amount can provide the particles having more pores. In a case where the volume average particle diameter is less than 1 μm, cohesion among the particles is likely to occur. In a case of more than 200 μm, the particles may become difficult to handle, depending upon intended use of the particles. The volume average particle diameter may be 1 µm, 2 µm, 3 µm, 10 µm, 20 µm, 50 µm, 75 µm, 100 µm, 150 µm, 180 µm, or 200 µm. The volume average particle diameter is preferably from 1 to 180 µm, and more preferably 2 to 150 µm. In a case where the linseed oil adsorption amount is lower than 150 mL/100 g, the particles blended with a cosmetic material or the like are likely to cause makeup to come off and are possibly difficult to keep makeup on. In a case of higher than 350 mL/100 g, other components are absorbed, possibly leading to low flowability and deteriorated handleability. The linseed oil adsorption amount may be 150 mL/100 g, 200 mL/100 g, 250 mL/100 g, 300 mL/100 g, 330 mL/100 g, or 350 mL/100 g. The linseed oil adsorption amount is preferably from 150 to 330 mL/100 g, and more preferably 150 to 300 mL/100 g.

Depending upon intended use of a product, the porous particles may vary in volume average particle diameter. For example, the volume average particle diameter may be properly selected depending upon intended use of a particles-containing product, such that for use in foundation, the volume average particle diameter may be from 3 to 20 µm; for use in skin scrubs, 100 to 200 µm; and for use in paints, 3 to 100 µm.

It is desirable that a ratio of a volume average particle diameter A to a number average particle diameter B of the porous particles stands at 1 to 6 (particle size distribution index; A/B), both of the diameters being determined by the Coulter counter method. In a case where the particle size distribution index is more than 6, the particles are widely and irregularly distributed, with the result that the scattered particles blended with a cosmetic material or the like may cause a rough texture of the cosmetic material. The particle size distribution index may be 1, 2, 3, 4, 5 or 6. The particle size distribution index is preferably from 1 to 4, and more preferably 1 to 3.

It is desirable that a ratio of an circle equivalent diameter (C) to the number average particle diameter (B) of the porous particles obtained by the method of the present invention stands at 1.1 to 2.0 (form index; C/B), the circle equivalent diameter corresponding to a diameter of a circle that is comparable to a projected area of one particle determined by an image analytical method, and the number average particle diameter being determined by the Coulter counter method. The porous particles of the present invention having the above-described range can be sufficiently recognized to have porosity with plural wrinkles (folds) as shown in FIGS. 2 to 6. In a case where this ratio is less than 1.1, the particles may not have the sufficient porosity. In a case where of more than 2.0, the particles may not have adequate particle strength. The ratio may be 1.1, 1.2, 1.3, 1.4, 1.5, 1.6, 1.7, 1.8, 1.9 or 2.0. The ratio is preferably from 1.1 to 19, and more preferably 1.1 to 1.8.

The Coulter counter method is to measure a particle diameter by detecting a change in electrical resistance while a particle passes through a fine pore. Thus it has been known that a true volume of a porous particle is measured, which is determined by eliminating a pore volume. The circle equivalent diameter is calculated by the image analytical method from an area of a projected image with fine-line surface asperities and a pore volume of the particle.

The following are suggested by calculation results: The closer to 1 the form index is, the closer to being spherical the particle is; and the farther from 1 the form index is, the more unevenness and the larger pore volume the particle has.

Figure 2:
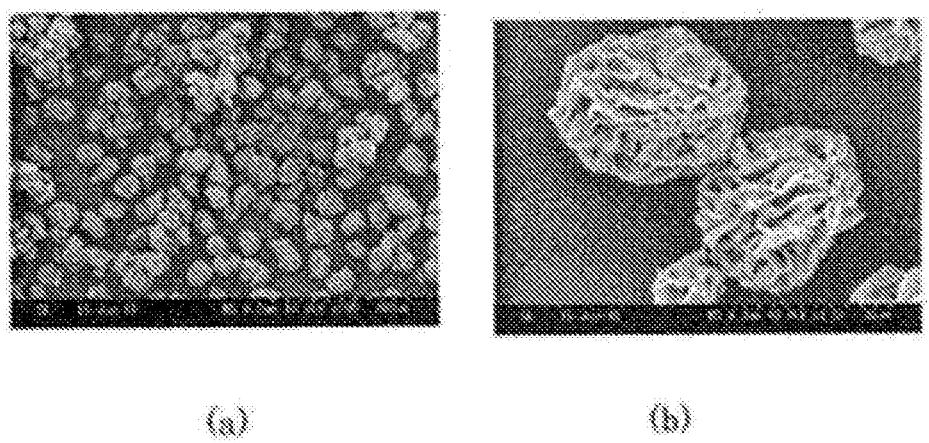
FIG. 2 shows photographs of porous resin microparticles in accordance with Example 1.
Figure 3:
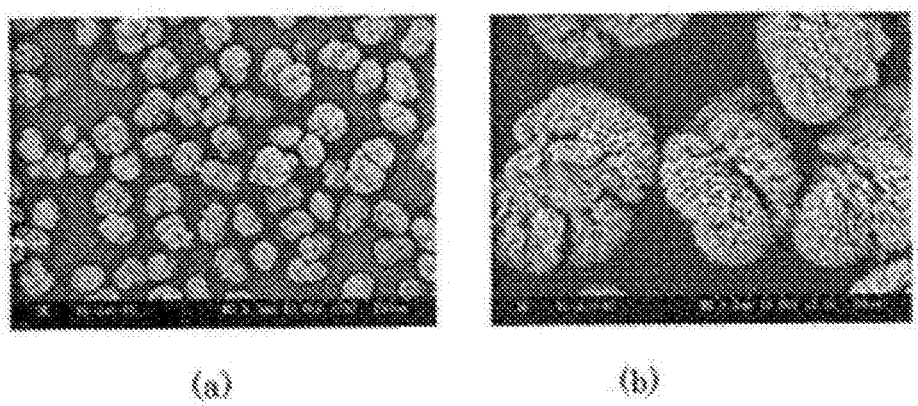

The porous particles having the above-described range of A/B and obtained by the manufacturing method of the present invention have large asperities as shown in, for example, FIGS. 1 and 2.

The porous particles may be used for formulation agents for cosmetics such as foundation, antiperspirants, and skin scrubs; various agents such as matte coating agents to be used in paints, rheological modifying agents, antiblocking agents, lubricating additives, light diffusing agents, auxiliary agents for sintering and forming fine ceramics, fillers for adhesive agents, and medical diagnostic agents; and additives used for molded articles such as automobile materials and construction materials.

Since the porous particles containing the polybutylene succinate or the polyhydroxyalkanoate as the main component are biodegradable, these particles may be used for bone repair materials and scaffold materials for cell regeneration.

EXAMPLES

Hereinafter the present invention will be described for more detail through the use of Examples; however, the present invention should not be limited only to these Examples. To begin with, measuring methods and evaluating methods used in the Examples and Comparative Examples will be described.

Measurement of Circle Equivalent Diameter and Sphericity

A flow-type particle image analyzer (trade name: FPIA™-3000S, manufactured by Sysmex Corporation) is used for the measurement.

The concrete measuring method is as follows: To 20 mL of ion-exchange water, 0.05 g of a surfactant as a dispersant, preferably alkyl benzene sulfonate, is added in order to obtain an aqueous surfactant solution. Subsequently, 0.2 g of a particle assemblage, which is a measuring object, is added to the aqueous surfactant solution; and the solution is irradiated with ultrasonic waves for 5 minutes with use of an ultrasonic disperser, as a disperser, manufactured by BRANSON (BRANSON SONIFIER 450 having an output power of 400 W and a frequency of 20 kHz); and the particle assemblage is subjected to a dispersion treatment so as to disperse the particle assemblage into the aqueous surfactant solution, obtaining a dispersion liquid to be used for the measurement.

To take the measurement, the above-mentioned flow-type particle image analyzer equipped with a (10×) regular objective lens is used; and the flow-type particle image analyzer uses a particle sheath (trade name: PSE-900A, manufactured by Sysmex Corporation) as a sheath fluid. The dispersion liquid to be used for the measurement, which was prepared as described above, is poured into the above-described flow-type particle image analyzer; and the particles are measured under the following measurement conditions:
Measurement mode: LPF measurement mode
Measurement range of a particle diameter: 10.00-153.5 µm
Measurement range of sphericity of particles: 0.5-1.0
Number of particles to be measured: 100

Before the start of the measurement, the flow-type particle image analyzer is subjected to an automatic focus adjustment with use of a suspension liquid of a standard polymer particle assemblage (such as 5200A, manufactured by Thermo Fisher Scientific, Inc. (which is prepared by diluting a standard polystyrene particle assemblage with ion-exchange water)). A number average particle diameter will be determined from one hundred (100) projected images obtained. Also, an circle equivalent diameter will be calculated with use of software equipped to the analyzer. A sphericity is indicated by a numerical value determined by dividing a circumference, which is calculated from a diameter of a perfect circle having the same projected area as an area of a photographed image of a particle, by a circumference of the photographed image of the particle.

Measurement of Volume Average Particle Diameter, Number Average Particle Diameter, and Particle Size Distribution Index—Coulter Counter Method A volume average particle diameter of particles is measured by a Coulter Multisizer™ 3 (manufactured by Beckman Coulter, Inc.). To take the measurement, an aperture is used that is calibrated according to a Multisizer™ 3 User's Manual issued by Beckman Coulter, Inc.

Depending upon a size of the particles to be measured, the aperture to be used for the measurement should be properly selected. The aperture may be properly selected as follows: In a case where an assumable volume average particle diameter of the particles to be measured is from 1 μmm or more to 10 μm or less, the aperture having a size of 50 μm is selected; in a case where an assumable volume average particle diameter of the particles to be measured is more than 10 μm and 30 μm or less, the aperture having a size of 100 μm is selected; in a case where an assumable volume average particle diameter of the particles is more than 30 μm and 90 μm or less, the aperture having a size of 280 μm is selected; and in a case where an assumable volume average particle diameter of the particles is mare than 90 μm and 150 μm or less, the aperture having a size of 400 μm is selected. If a measured volume average particle diameter differs from the assumed volume average particle diameter, the aperture may be changed to another aperture having a proper size, and the measurement is carried out again.

Depending upon the size of the selected aperture, a current (aperture current) and a gain should be properly set. In a case where the aperture having a size of 50 μm, a current (aperture current) should be set to be −800 and a gain should be set to be 4; in a case where the aperture having a size of 100 μm, a current (aperture current) should be set to be −1,600 and a gain should be set to be 2; and in a case where the aperture having a size of 280 μm and 400 μm, a current (aperture current) should be set to be −3,200 and a gain should be set to be 1.

As a sample to be measured, 0.1 g of particles are dispersed in 10 mL of a 0.1 wt % non-ionic aqueous surfactant solution with use of a touch mixer (manufactured by Yamato Scientific Co., Ltd., TOUCHMIXER MT-31) and an ultrasonic cleaner (manufactured by VELVO-CLEAR, ULTRASONIC CLEANER VS-150), obtaining a dispersion liquid. During the measurement, the dispersion liquid in a beaker is slightly stirred so as to prevent air bubbles from being formed in the dispersion liquid; and the measurement is terminated when 100,000 particles are measured. The volume average particle diameter and a number average particle diameter each are an arithmetic average obtained from a particle size distribution of the 100,000 particles, and these diameters are determined on a volumetric basis and a number basis, respectively.

A particle size distribution index of the particles is calculated by the following mathematical formula:

$$\text{particle size distribution index of particles} = \text{(volume average particle diameter}(A)\text{determined by Coulter counter method/number average particle diameter}(B)\text{determined by Coulter counter method)}$$

A form index of the particles is calculated by the following mathematical formula:

$$\text{form index of particles} = \text{(circle equivalent diameter }(C)\text{ determined by image analytical method/number average particle diameter }(B)\text{ determined by Coulter counter method)}$$

Measurement of Linseed Oil Adsorption Amount

A linseed oil adsorption amount of the particles is measured by a method using purified linseed oil instead of boiled linseed oil, in which the criteria for determining the end point of the method is changed (i.e., the criteria standard is changed to "stage where a paste (mixture of the particles and the purified linseed oil) starts flowing at a time when a measurement plate is placed to stand vertically"), by referring to a measuring method of JIS K 5101-13-2: 2004. The measurement of the linseed oil adsorption amount will be detailed below.

(A) Apparatuses and Devices

Measurement plate: flat and smooth glass plate larger than a size of 200×200×5 mm Palette knife (spatula): handled knife with a steel or stainless-steel blade Chemical balance (weigh scale): balance capable of measuring an object up to the order of 10 mg Burette: 10-mL burette stipulated by JIS R 3505: 1994

(B) Reagent

Purified linseed oil: linseed oil stipulated by ISO 150: 1980 (This time first-rate linseed oil (manufactured by Wako Pure Chemical Industries, Ltd.) is used.)

(C) Measuring Method (1) 1 g of the particles are placed on a central part on the measurement plate, 4 to 5 drops of the purified linseed oil are gradually dropped at a time from the burette onto the middle of the particles, and the particles and the purified linseed oil are thoroughly mixed and kneaded at every 4 to 5 drops with use of the palette knife.

(2) The above-described dropping and kneading are repeated; and once the particles and the purified linseed oil as a whole becomes entirely a hard putty-like lump, the lump is kneaded at every drop of the oil; and then once the paste (kneaded paste of the particles and the purified linseed oil) suddenly becomes soft and begins to fluidize by one last drop of the purified linseed oil, the end point is a point that the paste begins to fluidize.

(3) Determination of Fluidity

At the time when the paste suddenly becomes soft by one last drop of the purified linseed oil, and moves on the measurement plate vertically stood, the paste is determined as fluidized. In a case where the measurement plate is placed to stand vertically, but the paste does not move, another drop of the purified linseed oil is added to the paste.

(4) At the time when the paste arrives at the last stage, a consumed amount of the purified linseed oil is read out as a decreased amount of the fluid volume in the burette.

(5) One measurement should be completed within 7 to 15 minutes; and in a case where the measurement time exceeds 15 minutes, a remeasurement should be carried out; and time measured at the end point is recorded, which should be within the specified time.

(D) Calculation of Linseed Oil Absorption Amount

A linseed oil absorption amount per 100 g of a sample is calculated by the following formula:

$$O = (V/m) \times 100$$

wherein O: linseed oil absorption amount (mL/100 g); in weight of the particles (g); and V: consumed volume of the purified linseed oil (mL)

Measurement of Melting Point of Resin

A melting point of the resin is measured by a method described in JIS K 7122: 2012 "Testing Methods for Heat of Transition of Plastics". However, a sampling method and temperature conditions are specified as follows. An aluminum measuring container is filled with about 6 mg of a sample at its bottom with use of a differential scanning calorimeter, DSC 6220 (manufactured by SII NanoTechnology, Inc.), in such a way as not to have neither clearance nor space in the bottom of the container; and the sample is heated from 30° C. to 230° C. (1st Heating) at a nitrogen gas flow rate of 20 mL/min and left for 10 minutes, is then cooled from 230° C. to 30° C. (Cooling) and left for 10 minutes, and subsequently is heated from 30° C. to 230° C. (2nd Heating), obtaining a DSC curve. A rate of all the heating and the cooling is 10° C./min, and alumina is used as a reference material. In the present invention, a melting point indicates a value that is read out from a top of a melting peak temperature observed during 2nd Heating with use of software equipped to the calorimeter.

Measurement of Light Scattering Index (i) Measurement of Reflected Light Intensity Distribution Diffuseness of light reflected at a surface of the particles is evaluated by the following method.

A reflected light intensity distribution of the particles is measured by a 3D photometer (goniophotometer GP-200 manufactured by Murakami Color Research Laboratory Co., Ltd.) under conditions of room temperature of 20° C. and 65% relative humidity.

More specifically, (1) As illustrated in FIG. 1, a double-faced tape 3 (manufactured by ditto Denko Corporation, ORT-1), Which is cut into a 2-cm square, is pasted on a center of a black ABS resin plate 4 having a 2-mm thickness (manufactured by Takiron Corporation).

(2) Particles 2 are dropped onto an adhesive surface of the tape 3 on a black part of the black. ABS resin plate 4 with use of a funnel and a funnel support of an apparent density indicator (JIS K 5101-12-1-2004), and then the excess particles 2 on the adhesive face are blown off by compressed air of 0.05 to 0.1 MPa.

(3) The above-described black ABS resin plate 4 is placed on a flat glass plate; and another flat glass plate, which weighs 250 g and is cut into a 5-cm square, is placed on the spotting surface of particles 2; a load is applied to the particles 2, and this stays still for 1 minute. After that, the excess particles 2 on the above-described adhesive face are blown off by the compressed air.

(4) The same steps as in Sections (2) and (3) are repeated three times, and the test specimen thereby obtained is considered test specimen 1 to be subjected to a measurement of a reflected light intensity distribution. Reflected light of the obtained test specimen 1 is measured as follows. As illustrated in FIG. 1, light 5 emitted from a halogen lamp as a light source enters the test specimen 1 (particles 2) at an angle of −45° with respect to a normal line (0°) of the test specimen 1 (particles 2), and a light intensity distribution of the reflected light 6 is measured at reflection angles from −90° to +90° with use of the 3D photometer. To make the measurement, a position of the test specimen 1 is adjusted in such a way that all the incident light can enter the black part of the test specimen 1. The reflected light is detected by a photomultiplier having a spectral sensitivity from 185 to 850 nm and a highest sensitivity wavelength of 530 nm.

(ii) Calculation of Reflected Light Intensity at an Angle of 0° with Respect to 100 of Reflected Light Intensity at an Angle of +45°

Based on the reflected light intensity data (peak luminosity data) on the reflection angles of 0° and +45°, which are obtained from the measurement of the reflected light intensity distribution, a reflected light intensity (peak luminosity) at the reflection angle of 0° is obtained with respect to 100 of a reflected light intensity (peak luminosity) at the reflection angle of +45°. Based on the setting that the reflected light intensity at the reflection angle of +45° (specular direction) is 100, the closer to 100 the reflected light intensity is at the reflection angle of 0°, the better an effect of a soft focus is at a time of blending the particles with a cosmetic material. A light scattering index is calculated by the following formula:

light scattering index=(scattered light intensity at 0°)/(scattered light intensity at 45°)

The closer to 1 the light scattering index is, the higher the light-scattering property is without angular dependency.

Example 1

Into a 1,500-mL autoclave, 36 g of a polybutylene succinate (GS-Pla manufactured by Mitsubishi Chemical Corporation, part number: FZ-71PD, PBS, melting point: 113° C.) as a biodegradable resin and 1,164 g of 3-methoxy-3-methyl-1-butanol (Solfit Fine Grade manufactured by Kuraray Co., Ltd.) as a solvent were put; and a mixture was stirred at a heating and stirring temperature of 120° C. at a stirring and rotating speed of 600 rpm for 60 minutes.

After that, the mixture was left to be cooled (to 25° C. in 60 minutes) while the stirring and rotating speed was maintained; and then the content was taken out. The content was dehydrated, filtered, and dried, obtaining porous resin microparticles as shown in an electron micrograph of FIG. 2(a) and of FIG. 2(b). FIG. 2(a) shows the micrograph of the microparticles magnified 200 times, and FIG. 2(b) shows the micrograph of the microparticles magnified 1,500 times.

Example 2a

Porous resin microparticles as shown in an electron micrograph of FIG. 3(a) and of FIG. 3(b) were obtained in the same manner as Example 1, except that 60 g of a polylactic acid (TERRAMAC manufactured by Unitika Ltd., part number: TE-2500, melting point: 166° C.) as a biodegradable resin and 1,140 g of 3-methoxy-3-methyl-1-butanol (Solfit Fine Grade manufactured by Kuraray Co., Ltd.) were used; a heating and stirring temperature was 140° C.; and a mixture was rapidly cooled (to 25° C. in 30 minutes), instead of being left to be cooled. FIG. 3(a) shows the micrograph of the microparticles magnified 200 times, and FIG. 3(b) shows the micrograph of the microparticles magnified 1,500 times.

Example 3

Figure 4:
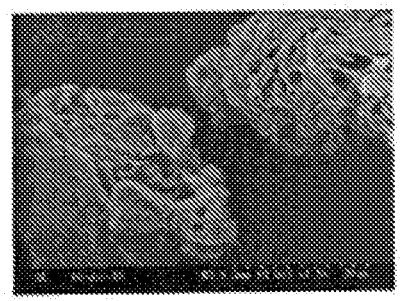
FIG. 4 shows a photograph of porous resin microparticles in accordance with Example 3.

Porous resin microparticles as shown in an electron micrograph of FIG. 4 were obtained in the same manner as Example 1, except that 90 g of a polybutylene succinate and 1,110 g of 3-methoxy-3-methyl-1-butanol (Soffit Fine Grade manufactured by Kuraray Co., Ltd.) were used; and a mixture was rapidly cooled (to 25° C. in 30 minutes), instead of being left to be cooled. FIG. 4 shows the micrograph of the microparticles magnified 1,000 times.

Example 4a

Porous resin microparticles were obtained in the same manner as Example 1, except that 4 polylactic acid (TER- RAMAC manufactured by Unitika Ltd., part number: TE-2500, PLA) as a biodegradable resin was used; and a heating and stirring temperature was 140° C.

Example 5a

Porous resin microparticles were obtained in the same manner as Example 1, except that a polylactic acid (TERRAMAC manufactured by Unitika Ltd., part number: TE-2500) as a biodegradable resin was used; a heating and stirring temperature was 140° C.; and a mixture was rapidly cooled (to 25° C. in 30 minutes), instead of being left to be cooled.

Example 6

Figure 5:
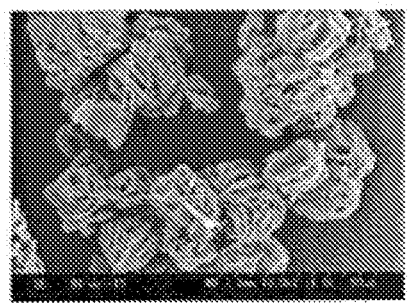
FIG. 5 shows a photograph of porous resin microparticles in accordance with Example 6.

Porous resin microparticles as shown in an electron micrograph of FIG. 5 were obtained in the same manner as Example 1, except that the mixture was rapidly cooled (to 25° C. in 30 minutes), instead of being left to be cooled. FIG. 5 shows the micrograph of the microparticles magnified 1,500 times.

Example 7a

Porous resin microparticles were obtained in the same manner as Example 1, except that 90 g of a polylactic acid (TERRAMAC manufactured by Unitika Ltd., part number: TE-2500) as a biodegradable resin and 1,110 g of 3-methoxy-3-methyl-1-butanol (Solfit Fine Grade manufactured by Kuraray Co., Ltd.) were used; a heating and stirring temperature was 140° C.; and a mixture was rapidly cooled (to 25° C. in 30 minutes), instead of being left to be cooled.

Example 8a

Porous resin microparticles were obtained in the same manner as Example 1, except that 90 g of a polylactic acid (TERRAMAC manufactured by Unitika Ltd., part number: TE-2500) as a biodegradable resin and 1,110 g of propylene glycol monopropyl ether (manufactured by Wako Pure Chemical Industries, Ltd.) as a solvent were used; and a heating and stirring temperature was 140° C.

Example 9a

Porous particles were obtained in the same manner as Example 1, except that 90 g of a polylactic acid (TERRAMAC manufactured by Unitika Ltd., part number: TE-2500) as a biodegradable resin and 1,110 g of propylene glycol monomethyl ether (manufactured by Wako Pure Chemical Industries, Ltd.) as a solvent were used; and a heating and stirring temperature was 140° C.

Example 10a

Figure 6:
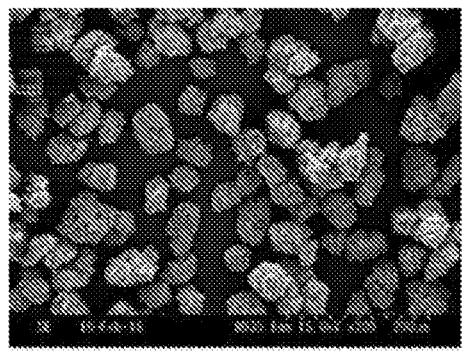

Porous resin microparticles as shown in an electron micrograph of FIG. 6 were obtained in the same manner as Example 1, except that 60 g of a copolymer of 3-hydroxybutyrate/3-hydroxyhexanoate (Kaneka Biopolymer AONILEX® manufactured by Kaneka Corporation, part number: X131A, melting point: 142° C.) as a biodegradable resin and 1,140 g of 3-methoxy-3-methyl-1-butanol (Solfit Fine Grade manufactured by Kuraray Co., Ltd.) were used; a heating and stirring temperature was 130° C.; and a mixture was rapidly cooled (to 25° C. in 30 minutes), instead of being left to be cooled. FIG. 6 shows the micrograph of the microparticles magnified 200 times.

TABLE 1

| | | Examples | | | | |
|---|---|---|---|---|---|---|
| | | 1 | 2a | 3 | 4a | 5a |
| Kinds of resin | PLA (g) | — | 60 | — | 36 | 36 |
| | PBS (g) | 36 | — | 90 | — | — |
| | Copolymer of 3-hydroxybutyrate/ | — | — | — | — | — |
| Kinds of solvent | 3-methoxy-3-methyl-1-butanol (g) | 1,164 | 1,140 | 1,110 | 1,164 | 1,164 |
| | Propylene glycol monopropyl ether (g) | — | — | — | — | — |
| | Propylene glycol monomethyl ether (g) | — | — | — | — | — |
| Cooling mode | | LC | RC | RC | LC | RC |
| Stirring and rotating speed (rpm) | | 600 | 600 | 600 | 600 | 600 |
| Heating and stirring temperature (° C.) | | 120 | 140 | 120 | 140 | 140 |
| Linseed oil absorption amount (mL/100 g) | | 215 | 211 | 154 | 245 | 300 |
| Volume average particle diameter A (μm) | | 34.45 | 46.7 | 55.32 | 32.16 | 61.93 |
| Number average particle diameter B (μm) | | 21.74 | 33.04 | 24.19 | 22.09 | 17.75 |
| Particle size distribution index (A/B) | | 1.58 | 1.41 | 2.29 | 1.46 | 3.49 |
| Circle equivalent diameter C | | 30.24 | 44.60 | 31.20 | 34.02 | 25.74 |
| Particle form index (C/B) | | 1.39 | 1.35 | 1.29 | 1.54 | 1.45 |
| Sphericity | | 0.95 | 0.93 | 0.94 | 0.91 | 0.93 |

| | | Examples | | | | |
|---|---|---|---|---|---|---|
| | | 6 | 7a | 8a | 9a | 10a |
| Kinds of resin | PLA (g) | — | 90 | 90 | 90 | — |
| | PBS (g) | 36 | — | — | — | — |
| | Copolymer of 3-hydroxybutyrate/ | — | — | — | — | 60 |
| Kinds of solvent | 3-methoxy-3-methyl-1-butanol (g) | 1,164 | 1,110 | — | — | 1,140 |
| | Propylene glycol monopropyl ether (g) | — | — | 1,110 | — | — |
| | Propylene glycol monomethyl ether (g) | — | — | — | 1,110 | — |

TABLE 1-continued

| Cooling mode | RC | RC | LC | LC | RC |
|---|---|---|---|---|---|
| Stirring and rotating speed (rpm) | 600 | 600 | 600 | 600 | 600 |
| Heating and stirring temperature (° C.) | 120 | 140 | 140 | 140 | 130 |
| Linseed oil absorption amount (mL/100 g) | 227 | 192 | 195 | 184 | 175 |
| Volume average particle diameter A (μm) | 45.00 | 63.39 | 125.3 | 110.8 | 51.69 |
| Number average particle diameter B (μm) | 21.91 | 14.26 | 46.75 | 43.60 | 21.63 |
| Particle size distribution index (A/B) | 2.05 | 4.45 | 2.68 | 2.54 | 2.4 |
| Circle equivalent diameter C | 25.11 | 18.38 | 65.91 | 58.86 | 32.18 |
| Particle form index (C/B) | 1.15 | 1.29 | 1.41 | 1.35 | 1.49 |
| Sphericity | 0.94 | 0.94 | 0.92 | 0.91 | 0.92 |

LC: Left to be cooled,
RC: Rapidly cooled

It is found from the above-described Examples that the biodegradable porous resin microparticles can be easily manufactured.

Example 4b

Figure 7:
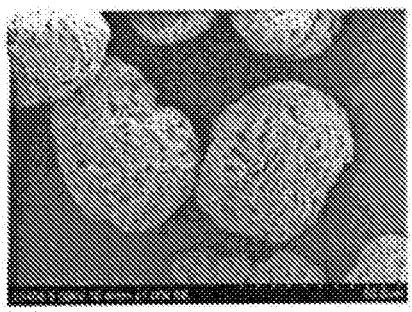
FIG. 7 shows a photograph of porous resin microparticles in accordance with Example 4.

Porous resin microparticles as shown in an electron micrograph of FIG. 7 were obtained in the same manner as Example 1, except that 120 g of a polybutylene succinate and 1,080 g of 3-methoxy-3-methyl-1-butanol (Solfit Fine Grade manufactured by Kuraray Co., Ltd.) were used; and a mixture was rapidly cooled (to 25° C. in 30 minutes), instead of being left to be cooled. FIG. 7 shows the micrograph of the microparticles magnified 1,000 times.

Example 5b

Figure 8:
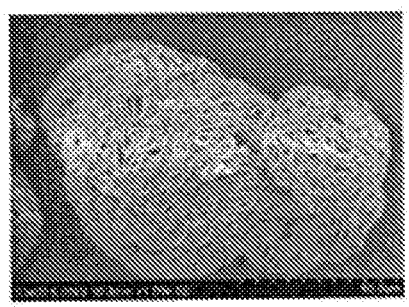
FIG. 8 shows a photograph of porous resin microparticles in accordance with Example 5b.

Porous resin microparticles as shown in an electron micrograph of FIG. 8 were obtained in the same manner as Example 1, except that 180 g of a polybutylene succinate and 1,020 g of 3-methoxy-3-methyl-1-butanol (Solfit Fine Grade manufactured by Kuraray Co., Ltd.) were used; and a mixture was rapidly cooled (to 25° C. in 30 minutes), instead of being left to be cooled. FIG. 8 shows the micrograph of the microparticles magnified 1,000 times.

The microparticles obtained from Examples 1, 3, 6, 4b and 5b were measured for a light scattering index.

TABLE 2

| | | Examples | | | | |
|---|---|---|---|---|---|---|
| | | 1 | 6 | 3 | 4b | 5b |
| Kind of PBS | FZ71PD (g) | 36 | 36 | 90 | 120 | 180 |
| Kind of solvent | 3-methoxy-3-methyl- | 1,164 | 1,164 | 1,110 | 1,080 | 1,020 |
| Cooling mode | | LC | RC | RC | RC | RC |
| Volume average particle diameter A (μm) | | 34.45 | 45.00 | 55.32 | 44.77 | 88.23 |
| Number average particle diameter B (μm) | | 21.74 | 21.91 | 24.19 | 31.31 | 54.13 |
| Particle size distribution index (A/B) | | 1.58 | 2.05 | 2.29 | 1.43 | 1.63 |
| Linseed oil absorption amount (mL/100 g) | | 215 | 227 | 154 | 252 | 185 |
| Circle equivalent diameter C (μm) | | 30.24 | 25.11 | 31.20 | 48.22 | 72.53 |
| Particle form index (C/B) | | 1.39 | 1.15 | 1.29 | 1.54 | 1.34 |
| Sphericity | | 0.95 | 0.94 | 0.94 | 0.93 | 0.91 |
| Reflected light intensity ratio | | 0.886 | 1.001 | 1.013 | 0.998 | 0.942 |
| Reflected light intensity (0°) | | 88.54 | 97.63 | 97.84 | 99.58 | 93.14 |
| Reflected light intensity (45°) | | 99.89 | 97.55 | 96.53 | 99.78 | 98.87 |

LC: Left to be cooled,
RC: Rapidly cooled

It is found from the above-described Examples that the polybutylene succinate-containing porous resin microparticles have the high light-scattering property.

REFERENCE SIGNS LIST

1: test specimen, 2: particles, 3: double-sided adhesive tape, 4: black ABS resin plate, 5: light, 6: reflected light

What is claimed is:

1. Porous resin microparticles containing polybutylene succinate or polyhydroxyalkanoate as a main component, wherein the porous resin microparticles have a particle form index of 1.1 to 2.0, wherein the particle form index is a circle equivalent diameter (C) of the porous resin microparticles divided by a number average particle diameter (B) of the porous resin microparticles.

2. Porous resin microparticles according to claim 1, wherein a volume average particle diameter (A) determined by a Coulter counter method is 1 to 200 μm, and a particle size distribution index (volume average particle diameter (A)/number average particle diameter (B)) is 1 to 6.

3. Porous resin microparticles according to claim 1, having plural wrinkles.

4. Porous resin microparticles according to claim 1, wherein the porous resin microparticles have a linseed oil absorption amount of 150 to 350 mL of linseed oil per/100 g of porous resin microparticles.

5. Porous resin microparticles according to claim 1, wherein a reflected light intensity ratio is 0.886 to 1.013, wherein the reflected light intensity ratio is a reflected light intensity at a reflection angle of 0° divided by a reflected light intensity at a reflection angle of 45°.

6. Porous resin microparticles according to claim 1, useful for cosmetics.

7. Porous resin microparticles according to claim 1, useful for paints.

8. Porous resin microparticles according to claim 1, useful for bone repair materials.

9. Porous resin microparticles according to claim 1, useful for scaffold materials for cell regeneration.

10. A cosmetic material comprising the porous resin microparticles according to claim 1.

11. A coating material comprising the porous resin microparticles according to claim 1.

12. An absorptive and slow-release formulation comprising the porous resin microparticles according to claim 1.

\* \* \* \* \*